United States Patent
Zhang et al.

(10) Patent No.: US 11,674,137 B2
(45) Date of Patent: Jun. 13, 2023

(54) ADAPTOR FOR SEQUENCING DNA AT ULTRATRACE LEVEL AND USE THEREOF

(71) Applicant: HAPLOX BIOTECHNOLOGY (SHENZHEN) CO., LTD.

(72) Inventors: Xiaoni Zhang, Shenzhen (CN); Ming Liu, Shenzhen (CN); Guolin Zhong, Shenzhen (CN); Mingyan Xu, Shenzhen (CN)

(*) Notice: Subject to any disclaimer, the term of this patent is extended or adjusted under 35 U.S.C. 154(b) by 1007 days.

(21) Appl. No.: 16/304,136

(22) PCT Filed: May 27, 2017

(86) PCT No.: PCT/CN2017/086330
§ 371 (c)(1),
(2) Date: Nov. 22, 2018

(87) PCT Pub. No.: WO2017/202389
PCT Pub. Date: Nov. 30, 2017

(65) Prior Publication Data
US 2020/0063125 A1  Feb. 27, 2020

(30) Foreign Application Priority Data
May 27, 2016  (WO) ................ PCT/CN2016/083748

(51) Int. Cl.
| | | |
|---|---|---|
| C12N 15/11 | (2006.01) | |
| C12N 15/10 | (2006.01) | |
| C40B 50/06 | (2006.01) | |
| C40B 70/00 | (2006.01) | |

(52) U.S. Cl.
CPC .......... *C12N 15/11* (2013.01); *C12N 15/1065* (2013.01); *C40B 50/06* (2013.01); *C40B 70/00* (2013.01); *C12N 2310/122* (2013.01); *C12N 2320/10* (2013.01)

(58) Field of Classification Search
None
See application file for complete search history.

(56) References Cited

U.S. PATENT DOCUMENTS

| | | | | |
|---|---|---|---|---|
| 2005/0202490 A1* | 9/2005 | Makarov | .............. | C12Q 1/6827 435/6.12 |
| 2009/0068645 A1* | 3/2009 | Sibson | ................. | C12Q 1/6816 435/6.12 |
| 2014/0106360 A1* | 4/2014 | Hayden | ................ | C12Q 1/6869 435/6.12 |
| 2014/0329282 A1* | 11/2014 | Nelson | ................. | C12Q 1/6855 435/91.2 |
| 2015/0031042 A1* | 1/2015 | Wood | ................... | C12Q 1/6883 435/6.12 |

FOREIGN PATENT DOCUMENTS

CN  105442054 A  3/2016

OTHER PUBLICATIONS

Hangzhou (CN 105442054 Mar. 30, 2016 machine translation (Year: 2016).*
International Preliminary Report on Patentability Chapter I.

* cited by examiner

*Primary Examiner* — Katherine D Salmon
(74) *Attorney, Agent, or Firm* — Avek IP, LLC

(57) ABSTRACT

Disclosed is an adaptor for sequencing DNAs at ultratrace levels and its uses. The adaptor contains, from 5'terminus to 3'terminus, a Tag sequence, PolyNs, a first stem sequencing, a first loop sequence, dUTP(s), a second loop sequence, and a second stem sequence, wherein the second stem sequence is complementary to the first stem sequence when read in opposite directions, and the 5'terminus of the adaptor is phosphorylated. The adaptor is designed to form a hairpin structure itself in use and then ligated to a DNA molecule of interest, so that adaptor-adaptor ligation can be effectively avoided, eliminating the inefficient adaptor-DNA ligation problem. Such an adaptor is especially suitable for library construction and sequencing of DNAs at ultratrace levels, laying a good basis for accurate sequencing of ctDNAs.

8 Claims, 4 Drawing Sheets

Specification includes a Sequence Listing.

ADAPTOR FOR SEQUENCING DNA AT ULTRATRACE LEVEL AND USE THEREOF

TECHNICAL FIELD

The present application relates to nucleotic acid sequences, particularly adaptors for sequencing DNAs at ultratrace levels, and the use thereof.

BACKGROUND

In the 21$^{st}$ century, with the advances in DNA technologies, several international collaborative research projects, including Human Genome Project, 1000 Genome Project, Cancer Genome Atlas, and Meta-Hit (METAgenomics of Human Intestinal Tract), are in progress, and genome research has become a hot topic. The next-generation sequencing technology currently takes a dominant position in the market with improved throughput and speed, and the major platforms include Illumina, Roche, and etc. One commonly used next-generation sequencing technology is sequencing by synthesis. In conventional DNA library construction, Y-shaped adaptors are introduced to both ends of DNAs of interest, and then DNA sequences are enriched and amplified through PCR. However, such adaptors along with the traditional amplification method are likely to cause extra errors in sequencing. On the other hand, with the development of genetic engineering, researchers demand higher accuracy and sensitivity in sequencing.

In 1947, Mandel and Metais discovered a kind of cell-free DNA in body fluids such as blood, synovial fluid and cerebrospinal fluid, as DNA-protein complexes or free DNAs. Then, in 1980s, Leon et al. found that tumor-bearing patients had higher DNA levels in serums than normal people. Further, it was reported that oncogene mutations determined in primary tumors were also found in plasma and serum of tumor-bearing patients. Such DNAs in the circulating serum of cancer patients were referred to as circulating tumor DNAs (abbreviated as ctDNA). ctDNAs were released from virable tumor cells or dying cells in progress of apoptosis into the circulatory system, which can be well recognized, quantitated and traced. Thus, in theory, gene mutations in early-stage tumor patients can be conveniently determined by simply testing ctDNAs in the circulating blood plasma, providing accurate information for cancer diagnosis and cancer-targeting medicament application.

However, ctDNA-based detection has not been widely used. The low amount of ctDNAs in the circulating blood remained as the major obstacle. As tumors progress, the blood ctDNA levels increase. However, even in advanced-stage cancer patients, the ctDNAs account for only 1% of the total cell-free DNAs. In early-stage cancer patients, the percentage of the blood ctDNAs is as low as 0.01%.

Currently employed library construction methods mainly involve use of Y-shaped adaptors. During the ligation of the Y-shaped adaptors to DNAs of interest, adaptor-adaptor ligation is likely to occur, especially when DNAs of interest are present at trace levels, which decreases ligation efficiency of Y adaptors to target DNAs, making it hard to detect ctDNAs present at low levels, and lowering detection accuracy and specificity. In this respect, urgently needed is certain technique for improving detection accuracy and specificity so as to remove the technical barrier to ctDNA capture and sequencing.

SUMMARY OF THE INVENTION

The present invention aims to provide a novel adaptor especially suitable for sequencing DNAs at ultratrace levels. The present invention also relates to use of the adaptor.

To accomplish the above-mentioned objective, the following technical solutions are adopted in the instant application.

In one aspect, the present application discloses an adaptor used for sequencing DNAs at ultratrace levels, comprising, from 5'terminus to 3'terminus, a Tag sequence, polyNs, a first stem sequence, a first loop sequence, dUTP(s), a second loop sequence and a second stem sequence. The second stem sequence is complementary to the first stem sequence in nucleotide sequence when read in opposite directions, and the 5'terminus of the adaptor is phosphorylated.

The Tag sequence, used for locating the adaptor and determining the starting position of the identification marker, is 3 to 4 bp in length. The Tag sequence is kept constant or unchanged for all adaptors or a certain group of adaptors. The polyN sequence is a random segment of 6 to 12 bp, used as a unique identification marker for the adaptor. The first and the second stem sequences are complementary, and base pair during annealing to form a hairpin/stem-loop structure, with the first loop sequence, dUTP(s) and the second loop sequence form the loop part of the hairpin structure. The primers for library construction are designed against the first and the second loop sequences, so that the target DNA fragments can be amplified after they are ligated by the adaptors. The dUTPs are introduced for cleavage of the adaptor at the specific site.

The adaptor of the present application is specially designed. It has some of its sequences paired and also its 3'terminus elongated in use, to form a hairpin structure. Then, two or more such hairpin-shaped adaptors are ligated to DNAs of interest. The adaptor with such special design may avoid adaptor-adaptor ligation as observed in Y-shaped adaptors, and is thus especially suitable for ligation to DNAs at ultratrace levels, such as ctDNA.

Any adaptor may have the desired effects as claimed in the present invention as long it possesses the above-mentioned structure. Spacer sequences of several bases in length may be inserted between each two adjacent parts of the adaptor, and the specific sequence of the spacers may depend on desires and will not be defined herein.

Preferably, the adaptor further contains a first index sequence between the first stem sequence and the first loop sequence.

Preferably, the adaptor further contains a second index sequence between the second stem sequence and the second loop sequence.

The first and the second index sequences are used to mark DNAs collected from different individuals, increasing the sequencing throughput. In other words, DNAs of different origins can be distinguished by index sequences. Thus, DNA sequencing may be performed for several subjects simultaneously, so that the sequencing throughput becomes higher. Those skilled in the art will appreciate that no index sequence is needed if only one subject is involved in DNA sequencing, or alternatively only a first index sequence or a second index sequence is required.

Preferably, the first and the second loop sequences are set forth in SEQ ID NOs.: 1 and 2, respectively, and the first and the second stem sequences are set forth in SEQ ID Nos.: 3 and 4, respectively.

SEQ ID No.: 1:
5'-ACACGTCTGAACTCCAGTCAC-3',

SEQ ID No.: 2:
5'-AATGATACGGCGACCACCGAGATCTACACTCTTTCCCTACACGAC-3',

SEQ ID No.: 3:
5'-AGATCGGAAGAGC-3',

SEQ ID No.: 4:
5'-GCTCTTCCGATCT-3'.

The first and the second loop sequences in the adaptor of the present invention are arranged for convenience of DNA amplification and enrichment using PCR. After the adaptors are ligated to different DNA fragments of interest, DNA amplification can be performed by PCR using primers designed against these loop sequences. The unique struction design of the adaptor is the key point of the present invention, and the adaptors having the sequences set forth in SEQ ID NOs.: 1, 2, 3 and/or 4 are the exemplary ones in various embodiments and are not limiting.

In another aspect, the present application discloses the use of the adaptor of the present invention in sequencing library construction and in next-generation sequencing.

Although the adaptor of the present invention is designed for sequencing or library construction of DNAs at ultratrace levels, its application is not limited thereto. Generally speaking, the adaptor of the present invention can be utilized in common sequencing library construction and next-generation sequencing.

In a further aspect, the present application discloses a method for constructing a library for ctDNA sequencing, comprising the steps of
(a) subjecting a plurality of adaptors of the present invention to annealing and extension so as to form a hairpin structure in each adaptor,
(b) ligating the products obtained in step (a) to extracted ctDNAs,
(c) cleaving the products obtained in step (b) with a dUTP specific excising enzyme, and
(d) PCR amplifying the enzyme-treated products using primers to generate a ctDNA sequencing library,
wherein the primers are a forward primer and a reverse primer designed against the first and the second loop sequences, respectively.

Preferably, the forward primer is set forth in SEQ ID No.: 5 while the reverse primer is set forth in SEQ ID No.:6.

SEQ ID No.: 5:
5'-AATGATACGGCGACCACCGAGATCTACAC-3',

SEQ ID No.: 6:
5'-CAAGCAGAAGACGGCATACGTGACTGGAG-3'.

Preferably, for the annealing and extension in step (a), the annealing is performed at 95° C. for 10 min, 70° C. for 10 min, 65° C. for 10 min, 60° C. for 10 min, 55° C. for 10 min, 50° C. for 10 min, 45° C. for 10 min, 40° C. for 10 min and then 25° C. for 10 min, after which the extension is performed by adding dUTPs, DNA polymerases and a reaction buffer to form a hairpin structure in each adaptor.

In a further aspect, the present application discloses a ctDNA sequencing library constructed by the method of the present invention.

Also, the present application discloses a method for sequencing ctDNAs at ultratrace levels, comprising constructing a sequencing library using the method of the present invention, and then carrying out DNA sequencing.

With the technical solutions above, the present application provides certain advantageous effects.

In specific, the adaptors of the present invention, each designed with a hairpin structure forming sequence, form hairpins in use and are then ligated to DNAs of interest, to effectively avoid adaptor-adaptor ligation and thus address the inefficient adaptor-DNA ligation problem. The adaptors of the present invention are especially suitable for library construction and sequencing of DNAs at ultratrace levels, enabling accurate ctDNA identification.

DETAILED DESCRIPTION OF THE INVENTION

The present invention, in view of the adaptor-adaptor ligation problem found in ligation of Y-shaped adaptors to DNAs of interest, has designed a novel structured adaptor. When such an adaptor is used in, for example, sequencing, it is subject to annealing and extension first to form a hairpin structure and then ligated to a DNA molecule of interest, so as to avoid adaptor-adaptor ligation. This may eliminate bad influence of the adaptor-adaptor ligation on sequencing of DNAs at ultratrace levels. Thus, the adaptors of the present application are applicable to ultratrace leveled DNAs. In one embodiment of the present application, the adaptors of the present invention are adopted for ctDNA sequencing.

The present invention will be further described in detail with reference to the specific example and drawings. The example below is used to illustrate the present invention, and should not be construed as limiting.

Example

Figure 1:
FIG. 1 is a schematic diagram showing the structure of an adaptor sequence in an example of the present application.

An adaptor was designed in the present example as shown in FIG. 1. The adaptor contained a Tag sequence, polyNs, a first stem sequence, a first index sequence, a first loop sequence, dUTP(s), a second loop sequence, a second index sequence and a second stem sequence from 5'terminus to 3'terminus. The second stem sequence and the first stem sequence were complementary in nucleotide sequence when read in opposite directions, and the 5'terminus of the adaptor was phosphorylated. In FIG. 1, Rd1SP, Index1, SP1, U, SP2, Index2 and Rd2SP referred to the first stem sequence, the first index sequence, the first loop sequence, dTUPs, the second loop sequence, the second index sequence, and the second stem sequence, respectively.

Figure 2:
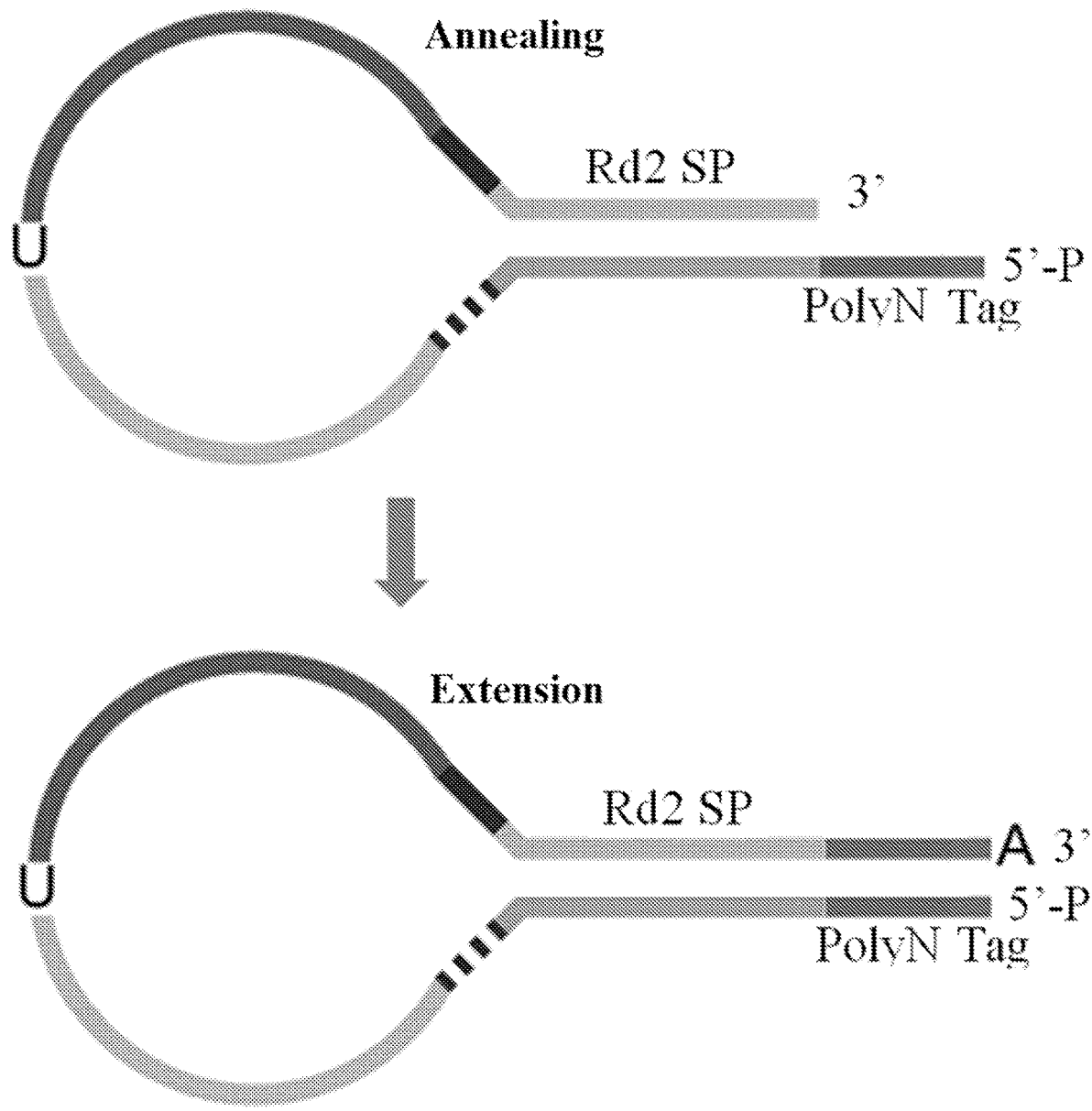
FIG. 2 is a schematic diagram showing pairing and extension of an adaptor sequence in an example of the present application.

The adaptor was firstly subject to annealing and extension, to form a hairpin structure, as shown in FIG. 2. Thereafter, the adaptor with a hairpin structure was ligated to a DNA molecule of interest.

In the present example, the Illumina sequencing platform was used, and the adaptor was designed as described above and shown below. As the sequencing was only performed on a sample collected from a single individual, no index sequence was arranged in the adaptor sequence. In other words, no first or second index sequence was in the adaptor sequence.

The adaptor sequence in this example was as follows.

```
                                           (SEQ ID No.: 7)
5'-P-ACTGNNNNNNNNNNNNNAGATCGGAAGAGC
     Tag  PolyN          first stem sequence ACACGTCTGAACTCCAGTCAC-U-
first loop sequence   dUTP AATGATACGGCGACCACCGAGATCTACACTCTTTCCCTACAC
               second loop sequence GACGCTCTTCCGATCT-3'.
 second stem sequence
```

Figure 3:
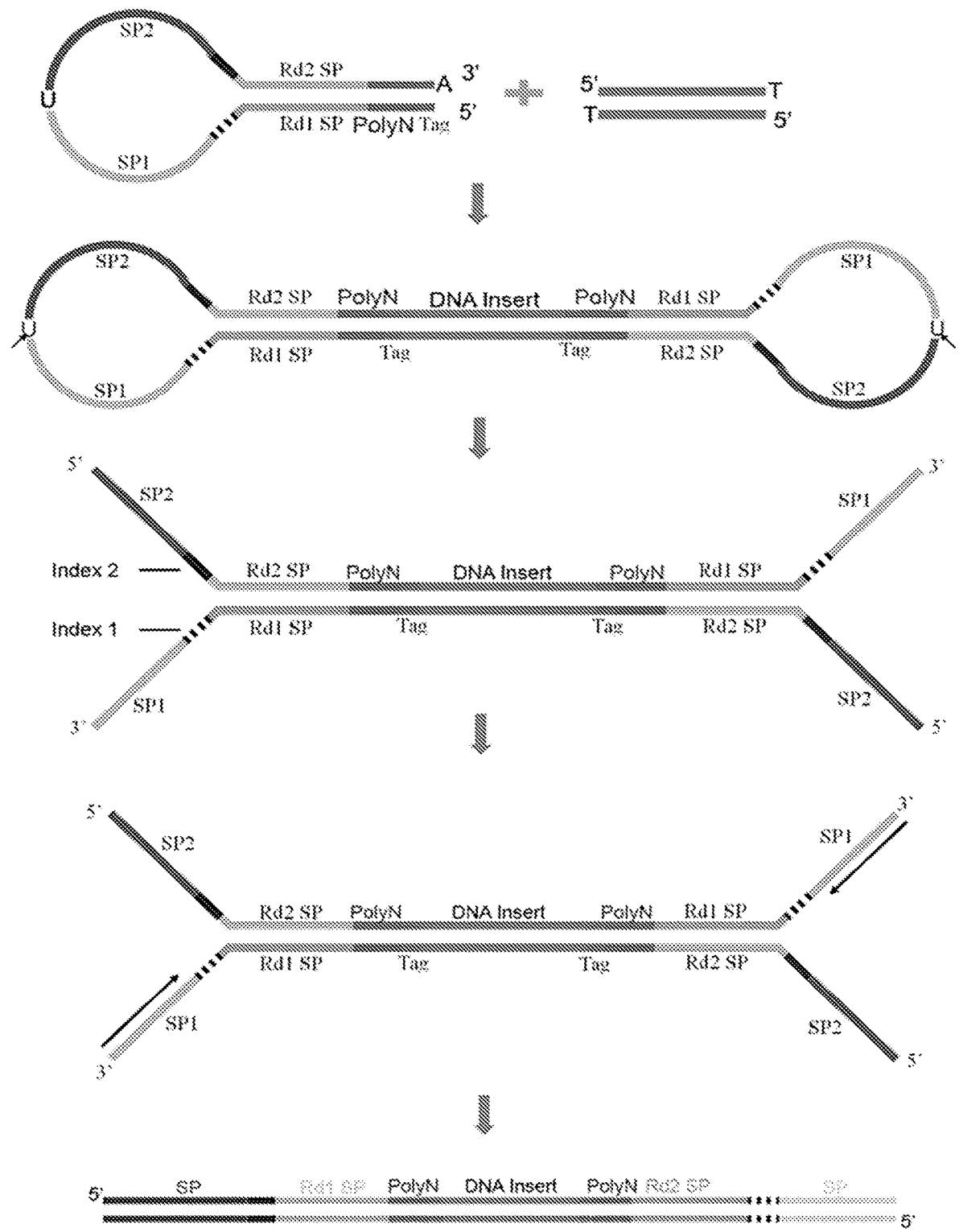
FIG. 3 is a schematic diagram showing construction of a sequencing library using the adaptors of the present invention in an example of the present application.

The method for constructing a sequencing library using a plurality of adaptors in this example, as shown in FIG. 3, specifically contained the steps of (1) allowing the synthetic adaptors to base pair to form a hairpin structure in each adaptor, and allowing the 3'terminus to extend against the Tag sequence with the polyN marker, (2) ligating the hairpin-shaped adaptors to both ends of each DNA of interest to form a closed loop structure, (3) cleaving the products obtained in step (2) with USER Enzyme specifically recognizing dUTP to form single-stranded structures on both ends, (4) PCR amplifying the DNAs of interest using primers designed against the first and the second loop sequences. High-fidelity DNA Polymerase I (Klenow Fragment), high-fidelity KAPA HiFi DNA polymerases, Phusion high-fidelity DNA polymerases, and Q5 high-fidelity DNA polymerases are commonly selected as the PCR polymerase in the example. Accordingly, in primer designs, the annealing temperature of the primers should match the working temperature of the DNA polymerase to be chosen.

Experiment 1

In this experiment, the 17$^{th}$ exon of EGFR (exon 17th) was tested, and adaptors were ligated to both ends of the DNA fragments in a ligation reaction. The sequence of EGFR 17$^{th}$ exon was set forth in SEQ ID No.: 8.

```
SEQ ID No.:8:
5'-GCCTAAGAT CCCGTCCATC GCCACTGGGA TGGTGGGGGC

CCTCCTCTTG CTGCTGGTGG TGGCCCTGGG GATCGGCCTC

TTCATGCGAA GGCGCCACAT CGTTCGGAAG CGCACGCTGC

GGAGGCTGCT GCAGGAGAGG GAG-3'
```

(1) Paring and Extension of Adaptor Sequence

The adaptors designed for the Illumina platform were used to sequence the DNA of SEQ ID No.: 7.

To each PCR tube was added 20 μL of 100 μM adaptors an 20 μL of water, and the resultant solution was mixed with fierce shaking and then subject to centrifugation. The adaptors' concentration became 50 μM. Annealing was performed.

The conditions for annealing were as follows.
95° C. for 10 min, with temperature lowering gradient being 100%,
70° C. for 10 min, with temperature lowering gradient being 5%,
65° C. for 10 min, with temperature lowering gradient being 5%,
60° C. for 10 min, with temperature lowering gradient being 5%,
55° C. for 10 min, with temperature lowering gradient being 5%,
50° C. for 10 min, with temperature lowering gradient being 5%,
45° C. for 10 min, with temperature lowering gradient being 5%,
40° C. for 10 min, with temperature lowering gradient being 5%,
25° C. for 10 min, with temperature lowering gradient being 100%.

Temperature-gradient annealing was adopted in this experiment for formation of hairpin structures, which was more effective and sensitive than conventional room temperature annealing.

The annealing was followed by extension. The reaction solution for extension, 60 μL in total volume, consisted of 40 μL of annealing products, 6 μL of 10×NEB buffer, 6 μL of 10 mM dNTP, 6 μL of 5 U/μL Klenowexo, and 2 μL of ddH$_2$O. Extension was performed at 37° C. for 60 min.

(2) Ligation of Adaptors to DNA Fragments to be Inserted

For the ligation of adaptors to DNAs of interest, the DNA ligase such as T4 liganse was used. The reaction solution, 20 μL in volume, consisted of 50 ng of DNA fragments to be inserted, 2 μL of 10× buffer, 1 μL of T4 liganse, and balance of ddH$_2$O. The ligation was performed overnight at 16° C., at which condition the ligation efficiency was proved to be the highest.

In this experiment, 17$^{th}$ exon, as the DNA fragment to be inserted between adaptors, was relatively small in size and thus can be directly ligated to adaptors. Similarly, in the detection of circulating cell-free DNAs (cfDNA) extracted from the blood, as such DNAs were about 160 bp in length, they can be directly subject to ligation, too. However, genomic DNAs, which were usually longer fragments, have to be fragmented before ligation to adaptors. For example, genetic DNAs extracted from blood, had to be fragmented by NEBNext®dsDNFragmentase before ligation to adaptors. The reaction solution for fragmentation, 20 μL in total volume, consists of 16 μL of genetic gDNAs, 2 μL of 10× buffer and 2 μL of fragmentase. The fragmentation should be performed at 37° C. for 30 min.

(3) Cleavage by dUTP specific excising enzyme

The Products Obtained in the Ligation Step were Recognized and Cleaved by a dUTP specific excising enzyme. In specific, 3 μL of NEBNext USER Enzyme was added to the DNAs after ligation, and the resultant mixture was incubated at 37° C. for 15 min.

Upon completion of cleavage, the resultant DNAs were purified. In the present experiment, DNAs in the reaction solution were purified using magnetic beads. Exemplary beads included AMPure XP magnetic beads, OMEGA magnetic beads, and the like. DNAs were incubated with beads for 10 to 15 min, where the DNAs and beads were mixed every 5 min to fully bind DNAs to beads. The, the magnetic beads were washed by 80% ethanol to enable binding of small DNA fragments to beads (not to wash away small fragments). The details were as follows.

Into 70 μL of the ligation reaction solution was added 120 μL of magnetic beads. The mixture was mixed evenly and incubated at room temperature for 15 min, during the incubation the mixture was gently mixed every 5 min. Then, each centrifugation tube filled with DNAs and beads was kept still in a magnetic stand at room temperature for 3 to 5 min. After all beads were attached to the magnetic stand, the supernatant was removed. Thereafter, 500 μL of freshly prepared 80% ethanol was added to the tube, and the genetic stand was gently and repeatedly turned to the upside-down status for 7 to 10 times and then kept still at room temperature for about 3 min. The supernatant was removed again, and ethanol was added for another washing. Then, all liquid was removed, and the centrifugation tubes were left to air dried in a 37° C. dry bath with tube caps removed, until the bead surfaces lost lustre. Nuclease-free water of 22 μL was added to the beads to sufficiently suspend the beads, and beads were then left still at room temperature for about 5 min to fully resolve DNAs in the water. The centrifugation tubes were placed on the magnetic stand again and left still at room temperature for 5 min. The supernatants were transferred to new Eppendorf tubes to obtain purified DNAs.

(4) Library Construction

Primers were designed against the first and the second loop sequences. The forward primer was set forth in SEQ ID No.: 5, and the reverse primer was set forth in SEQ ID No.:6.

The primers had sequences as below.

```
SEQ ID No.: 5:
5'-AATGATACGGCGACCACCGAGATCTACAC-3'

SEQ ID No.: 6:
5'-CAAGCAGAAGACGGCATACGTGACTGGAG-3'
```

KAPA 2G Robust HotStart polymerase was used in the PCR for amplification so as to construct sequencing library. The PCR amplification reaction solution, 25 μL in volume, consisted of: 12.5 μL of 2×KAPA 2G Robust HotStart Ready Mix, 1.25 μL of 10 μM forward primer, 1.25 μL of 10 μM reverse primer, 1 ng of DNA template, and balance of $H_2O_2$.

PCR reaction was performed at the following conditions: denaturation at 95° C. for 3 min; denaturation at 95° C. for 10 sec—annealing at 63° C. for 15 sec—extension at 72° C. for 10 sec, 35 cycles; final elongation at 72° C. for 5 min; final hold at 4° C.

(5) Sequencing

The PCR products were sequenced using Illumina as the sequencing platform.

Figure 4:
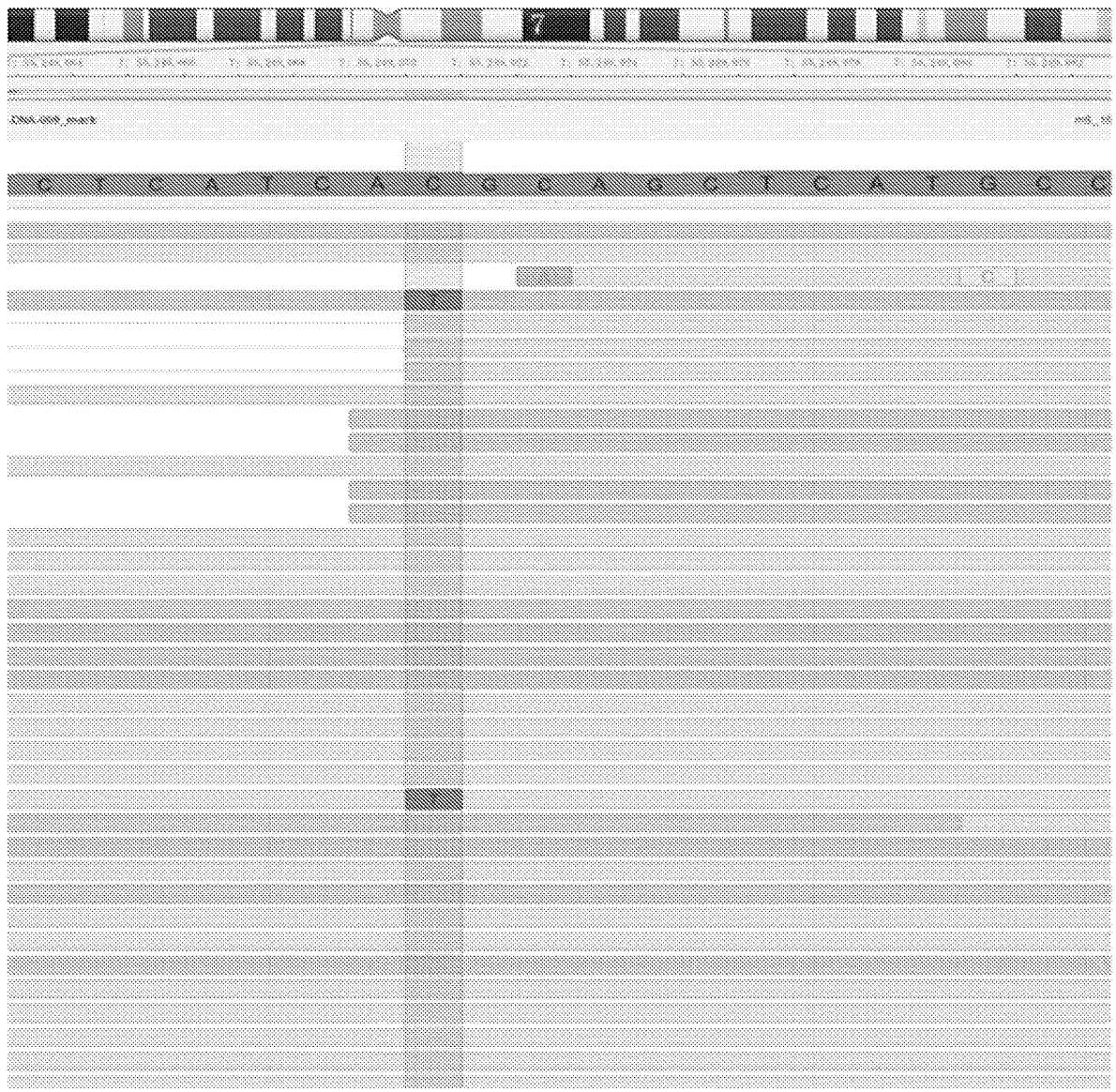
FIG. 4 is a diagram showing results of cfDNA mutation detection in Sample LC2014112 in an example of the present application.

Using the adaptors of the present example, the library construction method and the sequencing platform described above, cfDNAs from Sample LC2014112 were sequenced. In particular, 1 ng of cfDNAs from Sample LC2014112 were used for the library construction. The genetic testing revealed T790M mutation in the EGFR $20^{th}$ exon of this sample with an incidence of 0.208%, which induced resistance to EGFR-TKI therapy. The mutation identification results were shown in FIG. 4. FIG. 4 indicated that the base at chr7:55249071 of Chrosome 7, the site key to EGFR-TKI therapy, was turned to T from the intrinsic C in the DNAs from Sample LC2014112 where such a mutation induced resistance to EGFR-TKI therapy. According to the clinical test, resistance to EGFR-TKI therapy was observed in the individual from which Sample LC2014112 was collected, which was consistant to the above sequencing results, suggesting the accuracy of the identification in the present experiment.

As a comparative example, cfDNAs from the same sample, i.e., Sample LC2014112, were sequenced by using 1 ng of these cfDNAs in library construction where traditional Y-shaped adaptors were used for ligation. The results showed that no T790M mutation was identified in EGFR using the traditional sequencing method.

Therefore, it can be seen the sequencing method of the present example using the adaptors of the present invention in library construction had good detection sensitivity and accuracy, and was particularly suitable for detection of circulating cell-free DNAs. The method of the present example can effectively avoid errors introduced in DNA amplification during DNA library construction and sequencing, and present high-fidelity DNA information of the sample.

The foregoing describes the present invention in further details by ways of embodiments, but should not be construed as limiting the particular practice of the present invention thereto. Variations or modifications can be made by an ordinary skilled in the art to which the present invention pertains without departing from the scope and spirit of the present invention.

We claim:

1. An adaptor for sequencing DNAs at ultratrace levels, comprising, from 5' terminus to 3' terminus, in turn, a tag sequence, polyNs, a first stem sequence, a first loop sequence, dUTP(s), a second loop sequence, and a second stem sequence, wherein:
 the second stem sequence is complementary to the first stem sequence when read in opposite directions;
 the first loop sequence, the dUTP(s), and the second loop sequence form a portion of a loop and the dUTP(s) is/are located between the first loop sequence and the second sequence in the loop; and
 the 5' terminus of the adaptor is phosphorylated;
 wherein the first loop sequence, the second loop sequence, the first stem sequence, and the second stem sequence are set forth in SEQ ID Nos.: 1, 2, 3 and 4, respectively.

2. The adaptor according to claim 1, further comprising a first index sequence between the first stem sequence and the first loop sequence.

3. The adaptor according to claim 2, further comprising a second index sequence between the second loop sequence and the second stem sequence.

4. The adaptor according to claim 1, wherein the loop is formed during annealing.

5. An adaptor for sequencing DNAs at ultratrace levels, comprising, from 5'terminus to 3' terminus, in turn, a tag sequence, polyNs, a first stem sequence, a first loop sequence, dUTP(s), a second loop sequence, and a second stem sequence, wherein:
 the second stem sequence is complementary to the first stem sequence when read in opposite directions;
 the 5' terminus of the adaptor is phosphorylated; and
 the first loop sequence, the second loop sequence, the first stem sequence, and the second stem sequence are set forth in SEQ ID Nos.: 1, 2, 3 and 4, respectively.

6. The adaptor according to claim 5, further comprising a first index sequence between the first stem sequence and the first loop sequence.

7. The adaptor according to claim 6, further comprising a second index sequence between the second loop sequence and the second stem sequence.

8. The adaptor according to claim 5, wherein the first loop sequence, the dUTP(s), and the second loop sequence form a portion of a loop during annealing.

\* \* \* \* \*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: first loop

<400> SEQUENCE: 1
acacgtctga actccagtca c                                              21

<210> SEQ ID NO 2
<211> LENGTH: 45
<212> TYPE: DNA
<213> ORGANISM: Artificial Sequence
<220> FEATURE:
<223> OTHER INFORMATION: second loop
```

```
<400> SEQUENCE: 2
aatgatacgg cgaccaccga gatctacact ctttccctac acgac            45

<210> SEQ ID NO 3
<211> LENGTH: 13
<212> TYPE: DNA
<213> ORGANISM: Artificial Sequence
<220> FEATURE:
<223> OTHER INFORMATION: first stem

<400> SEQUENCE: 3
agatcggaag agc                                                13

<210> SEQ ID NO 4
<211> LENGTH: 13
<212> TYPE: DNA
<213> ORGANISM: Artificial Sequence
<220> FEATURE:
<223> OTHER INFORMATION: second stem

<400> SEQUENCE: 4
gctcttccga tct                                                13

<210> SEQ ID NO 5
<211> LENGTH: 29
<212> TYPE: DNA
<213> ORGANISM: Artificial Sequence
<220> FEATURE:
<223> OTHER INFORMATION: forward primer

<400> SEQUENCE: 5
aatgatacgg cgaccaccga gatctacac                               29

<210> SEQ ID NO 6
<211> LENGTH: 29
<212> TYPE: DNA
<213> ORGANISM: Artificial Sequence
<220> FEATURE:
<223> OTHER INFORMATION: reverse primer

<400> SEQUENCE: 6
caagcagaag acggcatacg tgactggag                               29

<210> SEQ ID NO 7
<211> LENGTH: 109
<212> TYPE: DNA
<213> ORGANISM: Artificial sequence
<220> FEATURE:
<223> OTHER INFORMATION: Nucleotide sequence of adaptor; N stands for
      deoxynucleotide.
<220> FEATURE:
<221> NAME/KEY: misc_feature
<222> LOCATION: (5)..(16)
<223> OTHER INFORMATION: n is a, c, g, or t

<400> SEQUENCE: 7
actgnnnnnn nnnnnnagat cggaagagca cacgtctgaa ctccagtcac uaatgatacg  60
gcgaccaccg agatctacac tctttcccta cacgacgctc ttccgatct            109

<210> SEQ ID NO 8
<211> LENGTH: 142
<212> TYPE: DNA
<213> ORGANISM: Homo sapiens

<400> SEQUENCE: 8
```

-continued

```
gcctaagatc ccgtccatcg ccactgggat ggtgggggcc ctcctcttgc tgctggtggt      60
ggccctgggg atcggcctct tcatgcgaag gcgccacatc gttcggaagc gcacgctgcg     120
gaggctgctg caggagaggg ag                                              142
```